US009683110B2

(12) United States Patent
Sokol et al.

(10) Patent No.: US 9,683,110 B2
(45) Date of Patent: Jun. 20, 2017

(54) MICROBIAL RESISTANT ROOF COATING AND SYSTEM

(71) Applicant: Garland Industries, Inc., Cleveland, OH (US)

(72) Inventors: David Sokol, Vermilion Township, OH (US); Jason Smith, Strongsville, OH (US)

(73) Assignee: Garland Industries, Inc., Cleveland, OH (US)

(*) Notice: Subject to any disclaimer, the term of this patent is extended or adjusted under 35 U.S.C. 154(b) by 0 days.

(21) Appl. No.: 14/968,969

(22) Filed: Dec. 15, 2015

(65) Prior Publication Data

US 2016/0102210 A1   Apr. 14, 2016

Related U.S. Application Data

(62) Division of application No. 14/044,309, filed on Oct. 2, 2013, now Pat. No. 9,303,168.

(60) Provisional application No. 61/711,501, filed on Oct. 9, 2012.

(51) Int. Cl.
C09D 5/02 (2006.01)
C09D 5/14 (2006.01)
C09D 7/12 (2006.01)
C09D 133/08 (2006.01)
A01N 25/10 (2006.01)
A01N 43/50 (2006.01)
A01N 43/52 (2006.01)
A01N 43/80 (2006.01)
A01N 55/02 (2006.01)
C08K 5/00 (2006.01)

(52) U.S. Cl.
CPC ............... C09D 5/14 (2013.01); A01N 25/10 (2013.01); A01N 43/50 (2013.01); A01N 43/52 (2013.01); A01N 43/80 (2013.01); A01N 55/02 (2013.01); C09D 7/1233 (2013.01); C09D 133/08 (2013.01); C08K 5/0058 (2013.01); C08L 2201/54 (2013.01); Y10T 428/31935 (2015.04)

(58) Field of Classification Search
CPC .......... C09D 5/14; A01N 43/50; A01N 43/52; A01N 43/80; A01N 55/02; A01N 25/10
USPC ....................................................... 524/556
See application file for complete search history.

(56) References Cited

FOREIGN PATENT DOCUMENTS

JP     2007126602 A   *   5/2007

OTHER PUBLICATIONS

Ishii et al., JP 2007-126602, May 24, 2007.*

* cited by examiner

Primary Examiner — Hui Chin
(74) Attorney, Agent, or Firm — Fay Sharpe LLP

(57) ABSTRACT

A roofing and/or siding material that reduces the incidence of undesired micro-organisms from entering into the air intake of air conditioner and/or heating systems of a building structure to thereby improve the quality of the air in the building structure.

17 Claims, 2 Drawing Sheets

MICROBIAL RESISTANT ROOF COATING AND SYSTEM

The present invention is a divisional application of U.S. patent application Ser. No. 14/044,309 filed Oct. 2, 2013, which in turn claims priority on U.S. Provisional Patent Application Ser. No. 61/711,501 filed Oct. 9, 2012, which is incorporated herein.

The present invention is directed to building structures that resist or inhibit microbial growth, particularly to roofing and/or siding systems that are formed of and/or are coated with components that resist or inhibit microbial growth, and more particularly to a roofing and/or siding system that includes one or more coating materials that resist or inhibit microbial growth and a method for forming such roofing and/or siding system and method for maintaining the efficacy of the roofing and/or siding system to resist or inhibit microbial growth.

BACKGROUND OF THE INVENTION

Mold and mildew are commonly associated with sickness, rashes and respiratory problems, among others. The contamination of a public facility with various types of mold and mildew can result in mild or severe health problems for one or more individuals located in such public facilities. One source of mold and mildew that is commonly overlooked is mold and mildew that grows and accumulates on the outside of a building structure. Such mold and mildew can subsequently be drawn into the air conditioning and/or heating system of the building through one or more air intake ducts that are commonly located on the roof of a building. Once the mold and mildew is drawn into the air intake of the air conditioning and/or heating system, any mold or mildew not collected by the filtration system is then spread throughout the interior of the building by the air conditioning and/or heating system.

Certain types of facilities, such as hospitals, can utilize a complex and expensive air filtration system to remove foreign material from the air circulated by the air conditioning and/or heating system. However, most public facilities such as indoor malls, schools, libraries, government buildings, office buildings, manufacturing plants, etc. do not use these complex and expensive air filtration systems. Generally, a standard air filter is used to remove larger particles from the air. However, these standard filters advertise prevention of over 99% of the mold and mildew from passing freely into the building space.

Standard roof systems, whether single ply, MB, BUR, asphalt shingled system, wood shingled system, concrete roofing system, metal roofing system, etc. do not resist or inhibit microbial growth on the roofing system. As such, over time, mold and mildew grow on the roofing system and can contaminate the air that is drawn into the air intake(s) of the air conditioning and/or heating system of a building.

In view of the current state of the art of roofing and/or siding systems, there is a need for a roofing and/or siding system and method for maintaining a roofing and/or siding system that resists or inhibits microbial growth on the roofing and/or siding system.

SUMMARY OF THE INVENTION

The present invention is directed to a roofing and/or siding system that includes a coating material that resists or inhibits microbial growth and method for forming such roofing and/or siding system and method for maintaining the efficacy of the roofing and/or siding system to resist or inhibit microbial growth. Although the invention will be particularly described with reference to a roofing and/or siding system, it will be understood that the invention has broader applications and can be used on other structures (e.g., plaza decks, exterior and interior walls, floors, sidewalks, patios, decks, stairs, steps, porches, etc.). The inclusion of one or more agents that inhibit or prevent microbial growth on and/or in the roofing and/or siding material can be used to prevent or inhibit the growth of fungus, mold, mildew and/or other types of undesirable micro-organisms on the roofing and/or siding material, thereby reducing the incidence of undesired micro-organisms being drawn into the air intake of air conditioner and/or heating units on the roof or other locations of a building. As such, the present invention is directed to a roofing and/or siding system that can improve the air quality for individuals located inside a building structure without the need for expensive and complex air filtration systems.

In one non-limiting aspect of the present invention, there is provided a material that can be used in a roofing and/or siding material that includes one or more agents that inhibit or prevent microbial growth on the roofing and/or siding material. The one or more agents that inhibit or prevent microbial growth can be added to the roofing and/or siding material when the roofing and/or siding material is being preformed and/or added to the roofing and/or siding material at the time the roofing and/or siding material is being formed or applied to a building structure.

In another and/or alternative non-limiting embodiment of the present invention, the one or more agents that inhibit or prevent microbial growth are coated on all or a portion of the outer surface of the roofing and/or siding material. The coating can be applied after the roofing and/or siding material has been preformed, and/or during and/or after the roofing and/or siding material has been applied to a building structure. The coating can be designed to be spray coated, painted, mop-applied, and the like. The coating can be a clear coating or include a color pigment to form a colored coating. The thickness of the coating on the roofing and/or siding material is non-limiting.

In still another and/or alternative non-limiting embodiment of the invention, there is provided a method for improving the air quality of air that is circulated in a building structure without the need for expensive and complex air filtration systems. The method includes the steps of installing a roofing and/or siding material on a building structure that is located near or adjacent to an air intake of an air conditioner and/or heating unit, and wherein the roofing and/or siding material includes and/or is coated with one or more agents that inhibit or prevent microbial growth on and/or in the roofing and/or siding material, thereby reducing the incidence of undesired micro-organisms being drawn into the air intake of the air conditioner and/or heating unit. The method can also optionally include the step of having a majority or all of the roofing and/or siding material that is installed on the building include and/or be coated with one or more agents that inhibit or prevent microbial growth on and/or in the roofing and/or siding material. The method can also optionally include the step of coating the roofing and/or siding material with a clear or colored coating that includes one or more agents that inhibit or prevent microbial growth during or after the roofing and/or siding material is installed on the building. The method can also optionally include the step of applying a coating that includes one or more agents that inhibit or prevent microbial growth to a portion or all of the air intake duct(s) of the air conditioner and/or heating unit.

The method can also optionally include the step of reapplying a coating on the roofing and/or siding material, which coating includes one or more agents that inhibit or prevent microbial growth, after a certain time period so as to maintain the efficacy of the coated roofing and/or siding material to inhibit or prevent microbial growth on the roofing and/or siding material. The method can also optionally include the step of reapplying a coating on a portion or all of the air intake duct(s) of the air conditioner and/or heating unit, which coating includes one or more agents that inhibit or prevent microbial growth, after a certain time period so as to maintain the efficacy of the coated air intake duct to inhibit or prevent microbial growth on the air intake duct. The method can also optionally include the step of inspecting the quality of the roofing and/or siding material that is installed on the building after a certain period of time to determine if repairs are required and/or if another coating layer, which coating includes one or more agents that inhibit or prevent microbial growth, should be applied to the roofing and/or siding material and/or air intake duct so as to maintain the efficacy of the coated roofing and/or siding material and/or air intake duct to inhibit or prevent microbial growth on the roofing and/or siding material and/or air intake duct.

In yet another and/or alternative non-limiting aspect of the present invention, there is provided a coating material that includes one or more agents that inhibit or prevent microbial growth that is formulated so that the coating material can be coated on a variety of substrates that include, but are not limited to, mineral cap sheet, flood coated rock, aluminum, Galvalume™, galvanized, Kynar™, steel, EPDM, PVC, TPO, coal tar mineral, white reflective elastomeric coating, and white reflective polyurethane coating.

In still yet another and/or alternative non-limiting aspect of the present invention, there is provided a coating material that is a clear coating.

In another and/or alternative non-limiting aspect of the present invention, there is provided a coating material that is a colored coating that includes some pigment (e.g., 0.1-5%, typically 0.2-0.8%). One non-limiting pigment can include titanium dioxide. The pigment in the coating material, when optionally used, can 1) provide the applicator some idea where the coating was applied (especially useful on a gray or darker surface) and/or 2) $TiO_2$ has been shown to impart UV stability when used in coatings, so once applied, the coating material would have some protection against UV degradation.

In another and/or alternative non-limiting aspect of the present invention, there is provided a coating material that includes a base coat composition and one or more anti-microbial additives. The base coat composition can include one or more resins. The one or more resins can include, but are not limited to, resins of acrylate, vinyl, styrene, vinyl acetate, ester and urethane polymers. In one non-limiting embodiment of the invention, the resin includes a water-based acrylic resin with a glass transition temperature ($T_g$) of about −5° F. to 20° F., typically about 0° F. to 10° F., and more typically about 3° F. to 7° F. The one or more anti-microbial additives can include, but are not limited to, methyl 2-benzimidazolecarbamate (BCM), 3-Iodo-2propynyl butyl carbamate (IPBC), and/or 3-(3,4-dichlorphenyl)-1,1-dimethylurea. The one or more anti-microbial additives can also or alternatively include one or more naturally occurring and/or synthetic proteins, polypeptides and/or peptides as a means to inhibit fungal and bacterial growth. Such naturally occurring and/or synthetic proteins, polypeptides and/or peptides can be used to target specific fungal species or bacterial species that are present on roof and/or siding surfaces; however, this is not required. Other non-limiting examples of anti-microbial additives that can also or alternative be used, are disclosed in U.S. Pat. No. 8,106,111; U.S. Pat. No. 7,939,500; U.S. Pat. No. 7,932,230; U.S. Pat. No. 7,736,423; US 2005/0058689; US 2006/0141003; US 2012/0097194; EP 0355765 and EP 2431429, all of which are incorporated herein by reference. The coating material can also optionally include a coloring agent that becomes clear or substantially clear once the coating dries and/or cures. The coloring agent can also be formulated to cause the dried and/or cured coating to be glossy and/or semi-glossy; however, this is not required. Non-limiting examples of such a color agent includes, but is not limited to, a pH indicator (e.g., phenol red, phenolphthalein, thiolphthalein, etc.).

In still another and/or alternative non-limiting aspect of the present invention, there is provided a clear coating material that includes a base coat composition and one or more anti-microbial additives. The base coat composition can include one or more resins. The one or more resins can include, but are not limited to, acrylate, vinyl, styrene, vinyl acetate, ester and/or urethane polymers. In one non-limiting embodiment of the invention, the resin includes an acrylic resin (e.g., a water-based acrylic resin) with a glass transition temperature ($T_g$) of about 0° F. to 90° F., typically 5° F. to 80° F., and more typically about 65-78° F. In one non-limiting formulation, the resin is 100% acrylic resin (e.g., Dow's EI-6000) that has a glass transition temperature ($T_g$) of about 72° F. to 78° F. The one or more anti-microbial additives can include, but are not limited to, dichloro-2-n-octyl-4-isothiazolin-3-one, sodium copper ethylenediaminetetraacetate, methyl 2-benzimidazolecarbamate (BCM), 3-iodo-2propynyl butyl carbamate (IPBC), and/or 3-(3,4-dichlorphenyl)-1,1-dimethylurea. The one or more anti-microbial additives can also or alternatively include one or more naturally occurring and/or synthetic proteins, polypeptides and/or peptides as a means to inhibit fungal and bacterial growth. Such naturally occurring and/or synthetic proteins, polypeptides and/or peptides can be used to target specific fungal species or bacterial species that are present on roof and/or siding surfaces; however, this is not required. Other non-limiting examples of anti-microbial additives that can also or alternative be used, are disclosed in U.S. Pat. No. 8,106,111; U.S. Pat. No. 7,939,500; U.S. Pat. No. 7,932,230; U.S. Pat. No. 7,736,423; US 2005/0058689; US 2006/0141003; US 2012/0097194; EP 0355765 and EP 2431429, all of which are incorporated herein by reference. The coating material can also optionally include a coloring agent that becomes clear or substantially clear once the coating dries and/or cures. The coloring agent can also be formulated to cause the dried and/or cured coating to be glossy and/or semi-glossy; however, this is not required. Non-limiting examples of such a color agent includes, but is not limited to, a pH indicator (e.g., phenol red, phenolphthalein, thiolphthalein, etc.).

In still yet another and/or alternative non-limiting aspect of the present invention, there is provided a base coat composition material that can optionally be applied to a roofing and/or siding material prior to the application of the clear coating in accordance with the present invention.

In another and/or alternative non-limiting aspect of the present invention, there is provided a method for applying a coating material (e.g., clear coating, non-clear coating) to a roofing and/or siding material that inhibits or prevents microbial growth on the roofing and/or siding material comprising the steps of:

a. Cleaning the surface of the roofing and/or siding material which is installed on a building structure, wherein the washing process can optionally including a power washing process with a detergent (e.g., Simple Green®), diluted bleach solution, etc., and then optionally a rinsing cleaning;

b. Optionally applying one or more coatings of a bio-resistant base coat composition to the roofing and/or siding material (e.g., spray coating, brush coating, etc.);

c. Applying one or more coatings of a bio-resistant clear or non-clear coating (e.g., spray coating, brush coating, etc.) that would retain its anti-microbial properties for a period of 3-36 months and typically about 12-24 months; and, d. Optionally applying a new a coating of a bio-resistant clear or non-clear coating after a certain period of time has passed (e.g. 3-36 months) since applying a previous coating of a bio-resistant clear or non-clear coating so as to maintain the efficacy of the coating on the roofing and/or siding material.

One non-limiting object of the present invention is to provide a coated roofing and/or siding material that reduces the incidence of undesired micro-organisms from entering into the air intake of air conditioner and/or heating systems of a building structure to thereby improve the quality of the air in the building structure.

Another non-limiting object of the present invention is to provide a coated roofing and/or siding material that includes and/or is coated with one or more agents that inhibit or prevent microbial growth on the roofing and/or siding material.

Still another and/or alternative non-limiting object of the present invention is to provide a clear or colored coating that includes one or more agents that inhibit or prevent microbial growth on the coated surface, and which coating can be applied onto a roofing and/or siding material.

Yet another and/or alternative non-limiting object of the present invention is to provide a clear or colored coating that includes one or more agents that inhibit or prevent microbial growth, and which coating can be spray painted onto a roofing and/or siding material.

Still yet another and/or alternative non-limiting object of the present invention is to provide a clear or colored coating that includes one or more agents that inhibit or prevent microbial growth and resist UV degradation, and which coating can be applied onto a roofing and/or siding material.

Another and/or alternative non-limiting object of the present invention is to provide a method for applying a clear or colored coating that includes one or more agents that inhibit or prevent microbial growth and/or resist UV degradation, and which coating can be applied onto a roofing and/or siding material.

Still another and/or alternative non-limiting object of the present invention is to apply a base coat composition to a roofing material that includes one or more agents that inhibit or prevent microbial growth and/or resists UV degradation, and then applying a clear coating on the base coat composition, which clear coating includes one or more agents that inhibit or prevent microbial growth and/or resist UV degradation.

Still yet another and/or alternative non-limiting object of the present invention is to provide a method for applying a clear or colored coating that includes one or more agents that inhibit or prevent microbial growth and/or resist UV degradation, and which coating can be applied onto a roofing and/or siding material, and subsequently maintaining the efficacy of the coating to inhibit or prevent microbial growth and/or to resist UV degradation.

These and other objects and advantages will become apparent to those skilled in the art upon reading and following the description taken together with the accompanying drawings.

BRIEF DESCRIPTION OF THE DRAWINGS

Reference may now be made to the drawings which illustrate various non-limiting embodiments that the invention may take in physical form and in certain parts and arrangement of parts wherein.

DETAILED DESCRIPTION OF THE NON-LIMITING EMBODIMENTS

Figure 1:
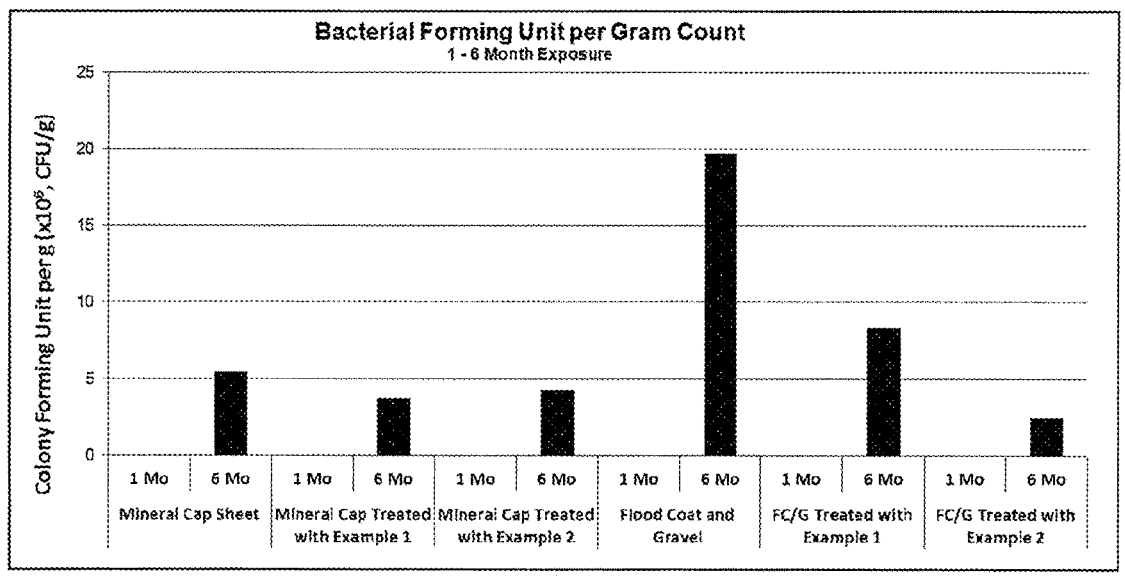
FIG. 1 is a graph illustrating bacterial growth on treated and untreated surfaces; and, FIG. 2 is a graph illustrating fungal growth on treated and untreated surfaces.

Referring now to the drawings, wherein the showings are for the purpose of illustrating preferred embodiments of the invention only and not for the purpose of limiting same, the present invention is directed to a roofing and/or siding system or other building structure (e.g., plaza decks, exterior and interior walls, floors, sidewalks, patios, decks, stairs, steps, porches, etc.) that includes a coating material that is formulated to resist or inhibit microbial growth (e.g., bacteria, fungus, etc.) and method for forming such roofing and/or siding system and method for maintaining the efficacy of the roofing and/or siding system to resist or inhibit microbial growth. The inclusion of one or more agents that inhibit or prevent microbial growth can be used to prevent or inhibit the growth of fungus, mold, mildew and/or other types of undesirable micro-organisms on the roofing and/or siding material or other building structures, thereby reducing the incidence of undesired micro-organisms from contacting individuals and/or from being drawn into the air intake of air conditioner and/or heating units on the roof or other locations of a building. As such, the present invention is particularly directed to a roofing and/or siding system that can improve the air quality for individuals located inside a building structure without the need for expensive and complex air filtration systems.

The one or more agents that inhibit or prevent microbial growth are typically coated on all or a portion of the outer surface of the roofing and/or siding material or other building structures. The coating can be applied after the roofing and/or siding material has been preformed, and/or during and/or after the roofing and/or siding material has been applied to a building structure. The coating can be designed to be spray coated, painted, mop-applied, and the like. The coating can be a clear coating or include a color pigment to form a colored coating.

The coating material that includes one or more agents that inhibit or prevent microbial growth can be coated on a variety of substrates that include, but are not limited to, mineral cap sheet, flood coated rock, aluminum, Galvalume™, galvanized, Kynar™, steel, EPDM, PVC, TPO, coal tar mineral, white reflective elastomeric coating, and white reflective polyurethane coating.

The coating material includes a base coat composition and one or more anti-microbial additives. The base coat composition can include one or more resins. The one or more resins can include, but are not limited to, resins of acrylate, resins of latex, vinyl, styrene, vinyl acetate, ester and/or urethane polymers. In one non-limiting embodiment of the invention, the resin includes a water-based acrylic resin with a glass transition temperature ($T_g$) of about −5° F. to 20° F., typically about 0° F. to 10° F., and more typically about 3° F. to 7° F. One non-limiting resin that can be used is an acrylic latex resin (e.g., Rhoplex EI-6000 from Dow Chemical, etc.). Other resins that can be used include, but are not limited to, Elastine 8556™, Lipacryl MB3640™, Primal 8349™, Primal AC-3001™, Primal AS-8000™, Primal EC-1791™, Primal MC-76LO™, Primal WL8179™, UCAR 161N™, UCAR CM 101™; RHOPLEX™ EI-2000 and RHOPLEX™ EI-5000. The one or more anti-microbial additives can include, but are not limited to, 4,5-dichloro-2-n-octyl-4-isothiazolin-3-one, sodium copper ethylenediaminetetraacetate, methyl 2-benzimidazolecarbamate (BCM); 3-Iodo-2propynyl butyl carbamate (IPBC); 3-(3,4-dichlorphenyl)-1,1-dimethylurea; 1,3-dihydroxymethyl-5,5-dimethylhydantoin; 1-hydroxymethyl-5,5-dimethylhydantoin; methyl 2-benzimidazolecarbamate; 3-Iodo-2-propynyl butyl carbamate; diuron[3-(3,4-dichlorphenyl)-1,1-dimethylurea); Cyclopropyl-N'-(1,1-dimethylethyl)-6-(methylthio)-1,3,5-triazine-2,4-diamine; octylisothiazolone; and quaternary ammonium compound. Non-limiting examples of commercially available anti-microbial additives that can be used include Bioban 200 and Rozone 2000™ (4,5-dichloro-2-n-octyl-4-isothiazolin-3-one and sodium copper ethylenediaminetetraacetate), Polyphase 662™ (Methyl 2-benzimidazolecarbamate, 3-Iodo-2-propynyl butyl carbamate and cyclopropyl-N'-(1,1-dimethylethyl)-6-(methylthio)-1,3,5-triazine-2,4-diamine); Polyphase 663™ (Methyl 2-benzimidazolecarbamate, 3-Iodo-2-propynyl butyl carbamate and Diuron[3-(3,4-dichlorphenyl)-1,1-dimethylurea)); Troysan 395™ (1,3-dihydroxymethyl-5,5-dimethylhydantoin and 1-hydroxymethyl-5,5-dimethylhydantoin); Bioban 100™ (octylisothiazolone; and quaternary ammonium compound). The one or more anti-microbial additives can also or alternatively include one or more naturally occurring and/or synthetic proteins, polypeptides and/or peptides as a means to inhibit fungal and bacterial growth. Such naturally occurring and/or synthetic proteins, polypeptides and/or peptides can be used to target specific fungal species or bacterial species that are present roof and/or siding surfaces; however, this is not required. Other non-limiting examples of anti-microbial additives that can also or alternative be used, are disclosed in U.S. Pat. No. 8,106,111; U.S. Pat. No. 7,939,500; U.S. Pat. No. 7,932,230; U.S. Pat. No. 7,736,423; US 2005/0058689; US 2006/0141003; US 2012/0097194; EP 0355765 and EP 2431429, all of which are incorporated herein by reference. The coating material can also optionally include a coloring agent that becomes clear or substantially clear once the coating dries and/or cures. The coloring agent can also be formulated to cause the dried and/or cured coating to be glossy and/or semi-glossy; however, this is not required. Non-limiting examples of such a color agent includes, but is not limited to, a pH indicator (e.g., phenol red, phenolphthalein, thiolphthalein, etc.). The coating material can include one or more dispersants or surfactants, coalescing solvent, defoamers, and/or deairators. Non-limiting surfactants that can be used include ethoxylated non-ionic surfactant (e.g., Carbowet 106™ (air products), Carbowet 109™ (air products), Carbowet 125™ (air products), Carbowet 138™ (air products), etc.); benzyl-polyethylene glycol (1,1,3,3-tetramethylbutylphenyl) ether, benzyl-polyethylene glycol tert-octylphenyl ether (e.g., Triton™ CF-10 (Dow Chemical), etc.). The coating material can include one or more defoamers. Non-limiting defoamers include 3-dimensional siloxane (e.g., DEEFO PI-35™ (Munzing), DEEFO PI50™ (Munzing), etc.); emulsion of polyether-siloxane (e.g., Tego Airex 902W™ (Evonik), etc.). The coating material can include one or more coalescing solvents (e.g., non-water solvents). Non-limiting coalescing solvents include ester alcohol (e.g., Texanol™ (Eastman Chemical), etc.). The coating material can include one or more deairators. Non-limiting coalescing deairators include siloxane deairator (e.g., Airase 8070™ (Air Products), etc.). The coating material can include one or more additional materials such as pH indicators, fillers, color pigments (e.g., titanium dioxide, etc.) and the like.

One general formulation of the coating is as follows:

| Raw Material | Weight % Range |
| --- | --- |
| Water | 10-40 |
| Resin | 20-75 |
| Anti-microbial Additive | 0.01-10 |
| pH Indicator | 0-1 |
| Dispersant or surfactant | 0-2 |
| Defoamer | 0-2 |
| pH adjuster (e.g., ammonia) | 0-1 |
| Coalescent or solvent | 0-2 |
| Color Agent or pigment | 0-25 |
| Filler | 0-70 |
| Deairator | 0-1 |
| Thickener | 0-3 |

One non-limiting clear coating formulation is as follows:

| Raw Material | Weight % Range | Example A Weight % |
| --- | --- | --- |
| Water | 20-40 | 29.4 |
| High Tg Acrylic (e.g., Dow's EI-6100 ™, etc.) | 60-75 | 68.7 |
| Anti-microbial Additive Blend (e.g., Troysan 395 ™ and of either Polyphase 663 ™ or Polyphase 662 ™, etc.) | 0.1-10 | 0.8 |
| pH Indicator | 0-1 | 0.2 |
| Dispersant or sufactant (e.g., Air Product's Carbowet 109 ™ or Dow's Triton CF-10 ™, etc.) | 0.1-1 | 0.6 |
| Defoamer (e.g., DEEFO PI-35 ™ or the like from Ultra Additives, Tego Airex 902W ™ from Evonik) | 0.05-0.8 | 0.4 |
| pH adjuster (e.g., ammonia, etc.) | 0-0.5 | 0.2 |
| Coalescent or solvent (e.g., Texanol ™, etc.) | 0.1-1 | 0.7 |

Another non-limiting clear coating formulation is as follows:

| Raw Material | Weight % Range | Example B Weight % |
| --- | --- | --- |
| Water | 20-40 | 28.7% |
| Acrylic Latex (e.g., Rhoplex EI-6000 ™, etc.) | 60-75 | 69.0% |
| Surfactant (e.g., Carbowet 109 ™, etc.) | 0.1-1 | 0.6% |
| Siloxane Deairator (e.g., Airase 8070 ™, etc.) | 0.05-1 | 0.2% |
| Coalescing Solvent (e.g., Texanol ™, etc.) | 0.2-2 | 0.7% |
| In-Can Bactricide (e.g., Troysan 395 ™, etc.) | 0.05-1% | 0.2% |
| Dry Film Anti-microbial/Antifungal Additive (e.g., Bioban 200 ™, etc.) | 0.05-4% | 0.6% |

One non-limiting non-clear coating formulation is as follows:

| Raw Material | Weight % | Example C Weight % |
|---|---|---|
| Water | 10-25 | 13.7 |
| Associative Thickener | 0.05-2 | 0.5 |
| Anti-microbial Additive Blend (e.g., Troysan 395 ™ and Bioban 200 ™ or Rozone 2000 ™, etc.) | 0.05-3 | 0.2-1 |
| pH Indicator | 0.01-0.5 | 0.05-0.1 |
| Dispersant or surfactant(Air Product's Carbowet 109 ™ or Dow's Triton CF-10 ™) | 0.05-1 | 0.4 |
| Defoamers (DEEFO PI-35 ™ or the like from Ultra Additives, Tego Airex 902W ™ from Evonik) | 0.05-0.8 | 0.3 |
| pH adjuster (e.g., ammonia, etc.) | 0.01-0.5 | 0.1 |
| Coalescent or solvent (Texanol ™) | 0.05-1 | 0.7 |
| Titanium Dioxide | 1-15 | 6.3 |
| Acrylic Latex | 20-55 | 42 |
| Filler | 5-60 | 34 |

One non-limiting method for applying a coating material (e.g., clear coating, non-clear coating) to a roofing and/or siding material that inhibits or prevents microbial growth on the roofing and/or siding material comprising the steps of:

a. Cleaning the surface of the roofing and/or siding material which is installed on a building structure, wherein the washing process can optionally including a power washing process with a detergent (e.g., Simple Green®), diluted bleach solution, etc., and then optionally a rinsing cleaning;

b. Optionally applying one or more coatings of a bio-resistant base coat composition to the roofing and/or siding material (e.g., spray coating, brush coating, etc.);

c. Applying one or more coatings of a bio-resistant clear or non-clear coating (e.g., spray coating, brush coating, etc.) that would retain its anti-microbial properties for a period of 3-36 months and typically about 12-24 months; and, d. Optionally applying a new a coating of a bio-resistant clear or non-clear coating after a certain period of time has passed (e.g. 3-36 months) since applying a previous coating of a bio-resistant clear or non-clear coating so as to maintain the efficacy of the coating on the roofing and/or siding material.

The effectiveness of the coating composition to inhibit or prevent bacterial and fungal growth on a treated rood surface is set forth below. Two formulations of the coated were tested. The two formulations are set forth as follows:

| Raw Material | Example of Raw Material | Example 1 wt % | Example 2 wt % |
|---|---|---|---|
| Water | | 29.2% | 28.8% |
| Acrylic Latex | Rhoplex EI-6000 ™ | 68.4% | 67.4% |
| Surfactant | Carbowet 109 ™ | 0.6% | 0.6% |
| Siloxane Deairator | Airase 8070 ™ | 0.2% | 0.2% |
| Coalescing Solvent | Texanol ™ | 0.7% | 0.7% |
| Defoamer | DEEFO PI-35 ™ | 0.1% | 0.1% |
| Bactricide | Troysan 395 ™ | 0.2% | 0.2% |
| Dry Film Anti-microbial/Antifungal Additive | Polyphase 662 ™ | 0.6% | 2.0% |

Figure 2:
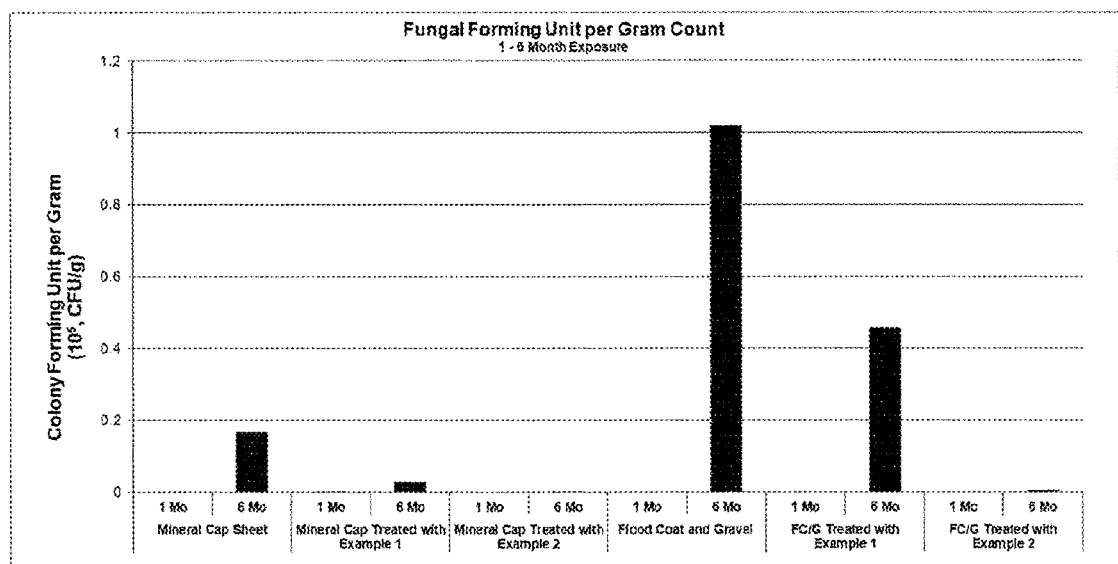

The non-limiting test procedure, which test results are illustrated in FIGS. 1 and 2, is described as follows:

Two sets of 3"×6" panels that included two types of typical (but non-limiting) roof surfaces were used in the experiment, namely a modified bitumen mineral-based cap sheet and a flood coat and graveled (FC/G) system consisting. Each panel included about 6-8 gal/100 ft$^2$ of asphalt or modified asphalt over a non-mineral (or "smooth") base sheet. Immediately after applying the hot asphalt or modified asphalt to the base sheet, aggregate in the form of pea gravel or river rock was dropped onto the still-molten asphalt surface. Five specimens of each representative surface type were left untreated (marked "Control"), two additional sets of five specimens from each surface type were coated on both sides with the coating formulations of Example 1 and Example 2. The panels were randomly arranged on stackable trays, which were then placed into a large bin containing enough water to be within approximately 1/8" from the bottom of the bottom tray. To encourage growth, an inocula solution was produced using several fungi and bacteria isolated from submitted actual roof specimens. The bin was sealed (not airtight) with a lid and placed under lamps that maintained the bin's daily interior temperature at between 95-100° F. Specimens were also sprayed with a solution of potato water and sugar to encourage fungal growth as well as a solution of salt-free chicken broth to encourage bacterial growth.

Small cuts (approx. 1"×1") were taken from each specimen at monthly intervals beginning at one month and continuing to six months. Testing of these specimens consisted of standard dilution of each followed by "spread plating" on a tryticase soy agar (TSA) to enumerate bacteria and a sabouraud dextrose agar (SDA) to enumerate fungal and mildew growth. The TSA was allowed to incubate 1-3 days at 86-95° F., and the SDA was allowed to incubate 2-5 days at 68-77° F. FIGS. 1 and 2 illustrate the averages of colony forming units (CFU) per gram of sample tested.

Referring to FIG. 1, there is a 20-30% reduction in bacteria colonies over mineral cap sheet and a more pronounced 57-87% reduction in bacterial colonies over flood coat and the gravel system when treated with the coating compositions of Examples 1 and 2. As illustrated in FIG. 2, there is an 80-97% reduction in fungal colonies formed over mineral cap sheet and a 55-99% reduction in fungal colonies over flood coat and gravel sheets treated with the coating compositions of Examples 1 and 2. FIGS. 1 and 2 graphically illustrate that the coating compositions of Examples 1 and 2 significantly reduce the growth of bacteria and fungi on roof systems as compared to a non-treated roof system.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A coating material that inhibits the growth of microbials on a surface of said coating material, said coating material includes water, a base coat composition, an anti-microbial additive and one or more additives selected from the group consisting of acrylic resin, pH indicator, surfactant, deairator, solvent, defoamer, thickener, filler, pH adjuster, and pigment, said base coat composition includes a resin material, said coating material includes by weight percent:

| | |
|---|---|
| Water | 20-40 |
| Acrylic resin | 60-75 |
| Anti-microbial additive | 0.1-10 |
| Defoamer | 0.05-0.8 |
| pH adjuster | 0-0.5 |
| pH indicator | 0-1 |
| Solvent | 0.05-2 |
| Surfactant | 0.05-1. |

2. The coating material as defined in claim 1, wherein said anti-microbial additive includes two different anti-microbial compounds.

3. The coating material as defined in claim 1, wherein said coating material includes by weight percent:

| | |
|---|---|
| Water | 28-30 |
| Acrylic resin | 65-70 |
| Anti-microbial additive | 0.4-1.5 |
| Defoamer | 0.2-0.6 |
| pH adjuster | 0-0.3 |
| pH indicator | 0-0.3 |
| Solvent | 0.5-0.9 |
| Surfactant | 0.5-0.9. |

4. The coating material as defined in claim 2, wherein said coating material includes by weight percent:

| | |
|---|---|
| Water | 28-30 |
| Acrylic resin | 65-70 |
| Anti-microbial additive | 0.4-1.5 |
| Defoamer | 0.2-0.6 |
| pH adjuster | 0-0.3 |
| pH indicator | 0-0.3 |
| Solvent | 0.5-0.9 |
| Surfactant | 0.5-0.9. |

5. The coating material as defined in claim 1, wherein said anti-microbial additive is 0.1-6 wt %, said solvent is 0.2-2 wt. %, said coating material further including 0.05-1 wt. % deairator.

6. The coating material as defined in claim 2, wherein said anti-microbial additive is 0.1-6 wt %, said solvent is 0.2-2 wt. %, said coating material further including 0.05-1 wt. % deairator.

7. The coating material as defined in claim 1, wherein said water is 25-30 wt. %, said acrylic resin is 66-72 wt. %, said anti-microbial additive is 0.4-1.2 wt. %, said solvent is 0.5-1 wt. %, said surfactant is 0.4-0.8 wt. %, said coating material further includes 0.1-0.3 wt. % deairator.

8. The coating material as defined in claim 2, wherein said water is 25-30 wt. %, said acrylic resin is 66-72 wt. %, said anti-microbial additive is 0.4-1.2 wt. %, said solvent is 0.5-1 wt. %, said surfactant is 0.4-0.8 wt. %, said coating material further includes 0.1-0.3 wt. % deairator.

9. The coating material as defined in claim 1, wherein said filler is 5-60 wt. %, said pH adjuster is 0.01-0.5 wt. %, said pH indicator is 0.01-0.5 wt. % said pigment is 1-15 wt. %, said solvent is 0.05-1 wt. %, and said thickener is 0.05-2 wt. %.

10. The coating material as defined in claim 2, wherein said filler is 5-60 wt. %, said pH adjuster is 0.01-0.5 wt. %, said pH indicator is 0.01-0.5 wt. %, said pigment is 1-15 wt. %, said solvent is 0.05-1 wt. %, and said thickener is 0.05-2 wt. %.

11. The coating material as defined in claim 1, wherein said anti-microbial additive is 0.2-1 wt. %, said filler is 20-40 wt. %, said pH adjuster is 0.01-0.5 wt. %, said pH indicator is 0.05-0.1 wt. %, said pigment is 4-10 wt. %, said solvent is 0.4-0.9 wt. %, said surfactant is 0.2-0.6 wt. %, and said thickener is 0.2-0.8 wt. %.

12. The coating material as defined in claim 2, wherein said anti-microbial additive is 0.2-1 wt. %, said filler is 20-40 wt. %, said pH adjuster is 0.01-0.5 wt. %, said pH indicator is 0.05-0.1 wt. %, said pigment is 4-10 wt. %, said solvent is 0.4-0.9 wt. %, said surfactant is 0.2-0.6 wt. %, and said thickener is 0.2-0.8 wt. %.

13. The coating material as defined in claim 1, wherein said anti-microbial additive is 0.4-2.5 wt. %, said defoamer is 0.05-0.4 wt. %, said solvent is 0.4-0.9 wt. %, said surfactant is 0.2-0.8 wt. %, said coating further including 0.1-0.5 wt. % deairator.

14. The coating material as defined in claim 2, wherein said anti-microbial additive is 0.4-2.5 wt. %, said defoamer is 0.05-0.4 wt. %, said solvent is 0.4-0.9 wt. %, said surfactant is 0.2-0.8 wt. %, said coating further including 0.1-0.5 wt. % deairator.

15. The coating material as defined in claim 1, wherein said resin includes a water-based acrylic resin with a glass transition temperature of about 0° F. to 90° F.

16. The coating material as defined in claim 1, wherein said anti-microbial additive includes one or more materials selected from the group consisting of 4,5-dichloro-2-n-octyl-4-isothiazolin-3-one; sodium copper ethylenediaminetetraacetate; methyl 2-benzimidazolecarbamate (BCM); 3-iodo-2-propynyl butyl carbamate (IPBC); 3-(3,4-dichlorophenyl)-1, 1-dimethylurea; 1,3-dihydroxymethyl-5,5-dimethylhydantoin; 1-hydroxymethyl-5,5-dimethylhydantoin; cyclopropyl-N'-(1,1-dimethylethyl)-6-(methylthio)-1,3,5-triazine-2,4-diamine; octylisothiazolone; and quaternary ammonium compound.

17. The coating material as defined in claim 1, wherein said surfactant is 0.05-1 wt. %, said surfactant including one or more compounds selected from the group consisting of ethoxylated nonionic surfactant; benzyl-polyethylene glycol (1,1,3,3-tetramethylbutylphenyl) ether, and benzyl-polyethylene glycol tert-octylphenyl ether.

* * * * *